United States Patent [19]

Etzweiler

[11] Patent Number: 4,954,150
[45] Date of Patent: Sep. 4, 1990

[54] DEVICE FOR BRANCHING GAS FLOWS

[75] Inventor: Franz Etzweiler, Greifensee, Switzerland

[73] Assignee: Givaudan Corporation, Clifton, N.J.

[21] Appl. No.: 254,990

[22] Filed: Oct. 7, 1988

[30] Foreign Application Priority Data

Oct. 8, 1987 [CH] Switzerland .......................... 3948/87

[51] Int. Cl.⁵ .............................................. B01D 15/08
[52] U.S. Cl. ......................................... 55/386; 55/197
[58] Field of Search ............................. 55/67, 197, 386

[56] References Cited

U.S. PATENT DOCUMENTS

| 3,357,233 | 12/1967 | Roof | 55/386 X |
| 3,408,793 | 11/1968 | Frazer | 55/197 |
| 3,422,665 | 1/1969 | Haase | 55/67 X |
| 3,494,174 | 2/1970 | Green et al. | 55/197 X |
| 3,536,452 | 10/1970 | Norton et al. | 55/197 X |
| 3,721,065 | 3/1973 | Robicheaux et al. | 55/67 |
| 4,442,217 | 4/1984 | Deans | 55/197 X |
| 4,470,832 | 9/1984 | Sugawara et al. | 55/197 |
| 4,478,720 | 10/1984 | Perrut | 55/67 X |
| 4,617,032 | 10/1986 | Wells | 55/67 |

FOREIGN PATENT DOCUMENTS

| 692119 | 8/1964 | Canada | 55/197 |
| 2520075 | 11/1976 | Fed. Rep. of Germany . | |
| 2840612 | 3/1980 | Fed. Rep. of Germany . | |
| 161967 | 4/1964 | U.S.S.R. | 55/67 |
| 0826110 | 12/1959 | United Kingdom . | |
| 2021969 | 12/1979 | United Kingdom | 55/197 |

Primary Examiner—Robert Spitzer
Attorney, Agent, or Firm—Robert F. Tavares; Linda A. Vag

[57] ABSTRACT

A device for branching gas flows, more particularly in a gas chromatography plant, the device having: an inlet branch connected to the output of a separating column; and two outlet branches which extend from a junction to subsequent parts of the plant, characterised in that one outlet branch is connected by way of a shutoff valve to a device producing a pressure lower than the pressure in the other outlet branch.

2 Claims, 2 Drawing Sheets

DEVICE FOR BRANCHING GAS FLOWS

BACKGROUND OF THE INVENTION

1. Field of the Invention

The invention concerns a device for branching gas flows, particularly in a gas chromatograph.

2. Background Art

In the field of gas chromatography it is known to place gas flow diverters in the flow path between two or more chromatography separating columns in order to enable the flow from a separating column to go at choice to one or more subsequent separating columns or detectors. In the known systems of this kind, the flow direction is diverted by the presence of auxiliary flow paths by means of which a positive pressure is produced in the particular branches it is required to close. The principle of this form of flow diversion is described in German patent 1,811,860. German patent specifications Nos. 2,806,123, 2,655,387 and 2,840,612 disclose other flow diverters based on the same principle.

It is a main purpose of these systems to be able to divert the flow direction without any contact occurring between the gas flow being controlled and valves. The point is that gas flows usually contain constituents which may be deposited in the valves. This may lead to two results—the valves become unserviceable, and the original gas flow composition is altered, thus falsifying the quantitative and qualitative determination of the substances present in the gas flow. Some of the known systems dealt with the problem of simplifying the complicated valve systems made necessary by the use of auxiliary flows. Nevertheless, all the known systems have disadvantages. For example, the auxiliary flows introduce impurities into the system and the flow dividers are of fairly complex construction requiring a considerable outlay for valves and valve controls.

It is an object of the present invention to simplify considerably the branching of gas flows.

SUMMARY OF THE INVENTION

The invention concerns a device for branching gas flows, more particularly in a gas chromatography, the device having: an inlet branch connected to the output of a separating column; and two outlet branches which extend from a junction to subsequent parts of the plant. The branching of the gas flow is simplified considerably in that one outlet branch is connected by way of a shutoff valve to means producing a pressure lower than the pressure in the other outlet branch. An embodiment of the invention described hereinafter with reference to the drawings, illustrates the advantages of the device.

BRIEF DESCRIPTIONS OF THE DRAWINGS

DESCRIPTION OF THE PREFERRED EMBODIMENTS

Figure 1:
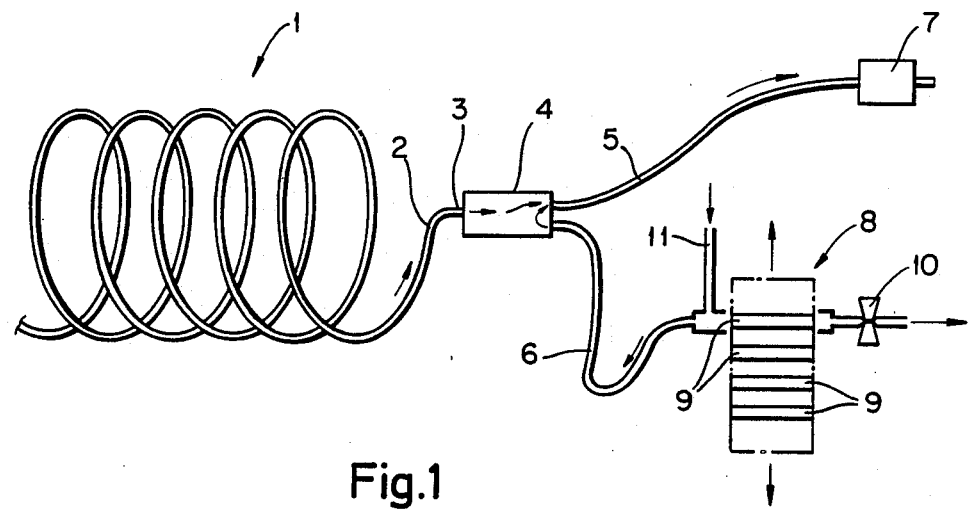
FIG. 1 is a diagrammatic view of a junction in one operative position.

As will be apparent from FIG. 1, a gas chromatography separating column 1 has an outlet 2 connected to an inlet branch 3 of a flow divider 4 as is now conventional for capillary columns.

The flow divider is made of glass and a quartz glass known under the commercial name of "Fused Silica". The separating columns are made of these two materials as well. Chemical inertia is therefore the same, so that all the substances which pass through the separating column without decomposition reach the interceptor intact. Also, since the cross-section in the two flow branches can be chosen freely, there is no loss of separating ability.

One outlet branch 5 is connected to a detector 7 from which the gas issues at atmospheric pressure. The detector is operative in conventional manner for observation of the components present in the gas flow.

The second outlet branch 6 extends to an interceptor 8 mainly comprising a series of adsorption or absorption tubes 9 adapted to be introduced alternately into the gas flow. The interceptor 8 will be described in greater detail hereinafter. The interceptor output is connected by way of a shutoff valve 10 to a vacuum. The valve 10 is a simple on-off valve, in the present case a pinch valve for flexible tubes.

A scavenging gas feed 11 is provided on the input side of the interceptor and extends into the outlet branch 6.

In the state shown in FIG. 1 the valve 10 is in the closed state—i.e., the interceptor 8 and the outlet branch 6 are isolated from the vacuum. Consequently, the gas flow from the separating column cannot reach the outlet branch 6 but flows to the detector 7. Also, a weak scavenging gas flow is fed into the output branch 6 through the scavenging gas inlet 11, flows to the flow divider and is combined therein with the main flow. The weak flow of scavenging gas ensures that the substances flowing from the column towards the detector cannot diffuse into the interceptor and contaminate the system therein.

Figure 2:
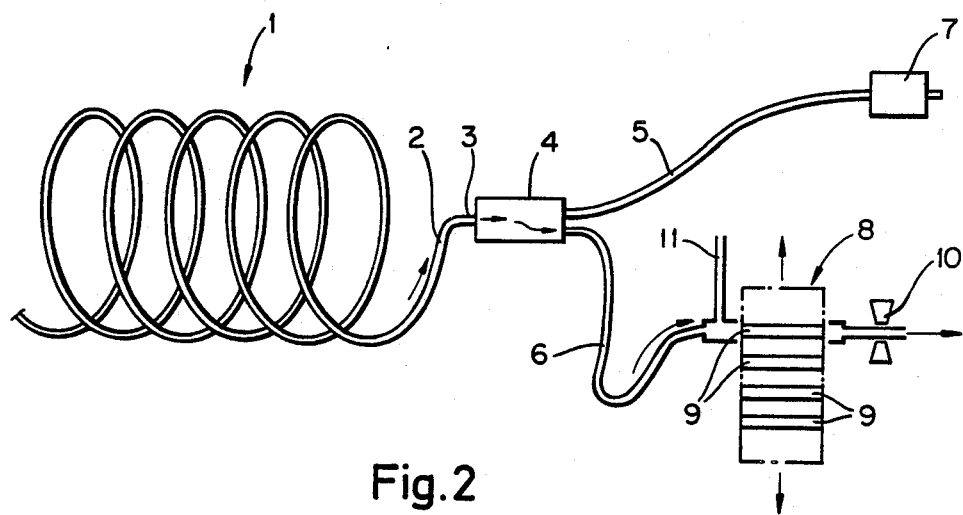
FIG. 2 shows the junction in the operative position.

When a substance required to be intercepted—i.e., a so-called GC peak—has reached the end of the column, the device is changed over to the state shown in FIG. 2 by the valve 10 being opened. The opening of the valve produces in the outlet branch 6 a pressure which is lower than the pressure in the outlet branch 5 and which diverts the gas flow through the branch 6 to the interceptor 8.

The extent to which the valve is opened can also be used to control the pressure difference between the two outlet branches so that the test flow can be supplied wholly or partly to the interceptor. Consequently, some of the flow can also flow via the detector for observation even after the changeover or diversion.

Figure 3:
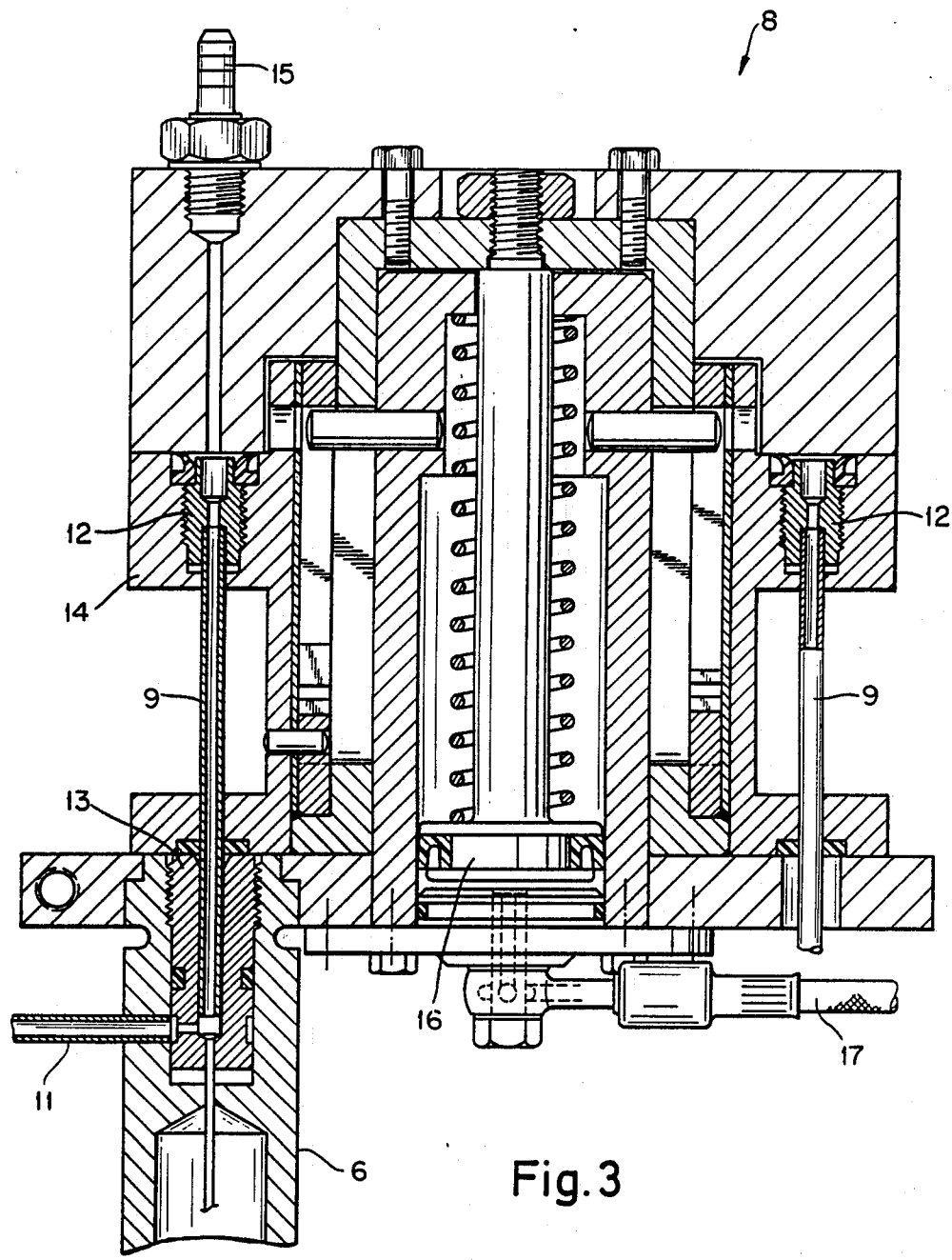
FIG. 3 is a section through the embodiment of the interceptor.

The interceptor 8 is shown in section in FIG. 3. It is mainly a mechanical device which comprises: the necessary number of adsorption tubes—up to 10 in the present embodiment—in an arrangement distributed uniformly along a cylindrical surface; and a drive for moving a required individual tube into the flow path. In the present embodiment the drive is pneumatic.

The tubes 9 are retained in a rotating drum 14 by appropriate retaining means 12, 13. The drum 14 has as many normal positions as there are tubes present. In each normal position a tube is present in the gas flow which comes from the connecting line to the flow divider—i.e., the outlet branch 6—and flows towards the vacuum by way of a connection 15 and the valve 10.

To change the tubes a pneumatic device comprising a piston 16 and a compressed air supply line 17 raises the drum 14 and so rotates it that a different tube moves into the gas flow. A mechanical click stop system ensures accurate location of the tubes.

The moving of the adsorption tubes alternately into the gas flow enables the advantage of the diverter to be fully used without valve combinations and without auxiliary flows to change over the flow directions.

As the embodiment shows, the device according to the invention is of much simpler construction than known devices for the same purpose. More particularly, a flow divider of very simple construction can be used, with advantages both for manufacturing costs and reliability of operation.

I claim:

1. A device for branching gas flows, more particularly in a gas chromatograph, the device having an inlet branch connected to the output of a separating column; two outlet branches which extend from a junction to subsequent parts of the plant, characterized in that a first outlet branch (6) is connected by way of a shutoff valve (10) to means producing a pressure lower than the pressure in the other outlet branch (5); an interceptor in the first outlet branch (6) between the junction and the valve (10); and a scavenging gas feed (11) between the junction and the interceptor extending into the first outlet branch (6).

2. A device according to claim 1, characterized in that the interceptor comprises a number of adsorption tubes and means for alternately connecting said adsorption tubes into the flow path.

* * * * *